(12) United States Patent
Feine

(10) Patent No.: US 7,959,438 B2
(45) Date of Patent: Jun. 14, 2011

(54) MOVABLE PIN ULTRASONIC TRANSDUCER

(76) Inventor: James Feine, Bellaire, TX (US)

( * ) Notice: Subject to any disclaimer, the term of this patent is extended or adjusted under 35 U.S.C. 154(b) by 992 days.

(21) Appl. No.: 11/308,190

(22) Filed: Mar. 10, 2006

(65) Prior Publication Data
US 2008/0015551 A1    Jan. 17, 2008

Related U.S. Application Data

(60) Provisional application No. 60/595,867, filed on Aug. 11, 2005.

(51) Int. Cl.
*A61C 1/07* (2006.01)
*A61C 3/03* (2006.01)
*A61C 3/025* (2006.01)

(52) U.S. Cl. ............ 433/119; 433/86; 433/125; 310/50; 310/17; 601/80; 606/169

(58) Field of Classification Search .............. 433/86, 433/119, 143; 601/80; 606/169, 171, 177, 606/178, 167, 170; 310/21, 30, 36, 47, 312, 310/12.01, 12.21, 12.22, 14, 24, 50, 15, 17, 310/23, 26, 118
See application file for complete search history.

(56) References Cited

U.S. PATENT DOCUMENTS

| | | | | |
|---|---|---|---|---|
| 3,201,670 A | * | 8/1965 | Myers | 318/125 |
| 3,645,255 A | * | 2/1972 | Robinson | 601/2 |
| 4,820,152 A | * | 4/1989 | Warrin et al. | 433/86 |
| 5,263,218 A | * | 11/1993 | Giuliani et al. | 15/22.1 |
| 5,382,162 A | * | 1/1995 | Sharp | 433/116 |
| 5,460,522 A | * | 10/1995 | Scarffe | 433/72 |
| 5,755,571 A | * | 5/1998 | Companion | 433/72 |
| 6,307,345 B1 | * | 10/2001 | Lewis | 318/696 |
| 6,752,629 B2 | * | 6/2004 | Suzuki et al. | 433/119 |
| 2003/0022129 A1 | * | 1/2003 | Rahman et al. | 433/119 |
| 2003/0083685 A1 | * | 5/2003 | Freeman et al. | 606/181 |
| 2003/0125645 A1 | * | 7/2003 | Rabiner et al. | 601/2 |
| 2006/0014119 A1 | * | 1/2006 | Bouneff | 433/118 |

* cited by examiner

*Primary Examiner* — Todd E Manahan
*Assistant Examiner* — Michael R Ballinger
(74) *Attorney, Agent, or Firm* — Marshall, Gerstein & Borun LLP

(57) ABSTRACT

An ultrasonic tool is disclosed with a handpiece (300, 500, 806) containing coils (304A-304D; 504A-504D; 804A-804B) that produce an electromagnetic field that vibrates a magnetic rod (102, 702A, 702B, 820) of a moveable pin transducer (MPT) 100 disposed within the handpiece. Ultrasonic vibrations are produced when the coils are selectively powered by an ultrasonic signal generator, which can include a stepper motor control apparatus (1300, 1400). A tip 106 can be removably attached to an MPT 100. A channel (708A, 708B) in the magnetic rod (700A, 700B) can allow fluidic communication with a handpiece fluid supply channel (310, 510). A method of vibrating a tool can include controllably energizing at least one electromagnetic coil contained within a handpiece to vibrate a magnetic rod and an attached tip. The method can include varying the energy to at least one of the electromagnetic coils with a stepper motor control apparatus.

33 Claims, 8 Drawing Sheets

MOVABLE PIN ULTRASONIC TRANSDUCER

CROSS REFERENCE TO RELATED APPLICATION

This application claims the benefit of my earlier application U.S. Ser. No. 60/595,867 filed Aug. 11, 2005.

BACKGROUND

This invention concerns the generation and utilization of ultrasonic energy as it applies to ultrasonic tools; specifically to an ultrasonic tool providing a tip connected to a movable magnetic rod vibrated by closely positioned electromagnetic coils in a handpiece.

In the past, ultrasonic energy for applications, for example, dental scaling, was generated by use of magnetostrictive, piezoelectric, ferritestrictive, or air driven elements. Each of these methods has one or more disadvantages: heat buildup, power-control, high voltage requirement, fragility, limited or fixed frequency, limited or fixed type of motion generated, or production expense. These disadvantages can limit the devices from performing their intended purposes.

In contrast, an electromagnet is a well known device in which magnetism is produced by electrical current. When current is passed through a wound coil of several turns, the coil is magnetized, and resultantly when no current is flowing through the coil, the coil is de-magnetized. A metallic member, for example, iron, can be disposed along the longitudinal axis of a coil to increase the electromagnetic force generated. The strength of the magnetic field produced by an electromagnet is affected by such factors as the number of coils used, the number of turns in each coil, the magnitude of the current, and the magnetic permeability of the metallic coil material. The presence of an optional metallic member, for example, an iron core, can also affect the strength of the electromagnetic field.

The general application of stepper motors is well known. The use and theory of controlling current flow to the coils of a stepper motor through the use of a stepper motor control apparatus, sometimes also referred to as a driver or translator, is well developed. A stepper motor converts pulses of electrical current into specific rotational movements. A stepper motor can allow a "one phase on" stepping sequence or a "two phase on" stepping sequence, for example. A stepper motor can be "half stepped" by inserting an off state between transitioning phases and can utilize bipolar and/or unipolar winding, as is known in the art. A representative example of a stepper motor control apparatus is disclosed in U.S. Pat. No. 6,307,345, incorporated by reference herein.

SUMMARY OF THE INVENTION

The current invention allows a stepper motor control apparatus to controllably energize electromagnetic coils in close proximity to a movable magnetic rod carrying an ultrasonic tip to create and/or control ultrasonic vibration in the tip.

The present invention solves the problems inherent in the prior art by allowing precision electromagnetic ultrasonic tools to be developed with the following advantages: (1) higher precision frequency control than available in the prior art; (2) significantly higher range of available frequency control than available in the prior art; (3) precise control of the vibratory pattern of the tools or tips; and/or (4) production of tools as described above in a cost-effective manner.

The present invention is directed to an ultrasonic tool providing a tip attached to a movable magnetic rod vibrated by electromagnetic coils in a handpiece. The electromagnetic coils are conductively connected to an ultrasonic signal generator that selectively energizes the coils to generate an electromagnetic field, which can be of varying geometry. The ultrasonic signal generator can include a stepper motor control apparatus to selectively energize the coils.

In one embodiment, the present invention provides an ultrasonic tool. The tool can include a handpiece containing coils capable of generating an electromagnetic field, a movable magnetic rod positioned adjacent the coils for displacement in response to the electromagnetic field, a tip rigidly attached to an end of the magnetic rod, and an ultrasonic signal generator operatively connected to the coils to generate the electromagnetic field.

In another embodiment, an ultrasonic tool includes a handpiece providing a well and containing at least one coil conductively connected to an ultrasonic signal generator to create an anisotropic electromagnetic field in the well, and a magnetic rod with a distal end comprising a tip and a proximal end moveably disposed at least partially within the electromagnetic field to vibrate the tip in response to the ultrasonic signal. The magnetic rod can have a fulcrum disposed between the proximal and distal ends and coupled to the handpiece at a distal end of the well. The magnetic rod can be tapered from a larger distal end to a smaller proximal end. A transverse cross-section of the magnetic rod can be ovate. A transverse cross-section of the well can be ovate.

In yet another embodiment, the ultrasonic signal generator can include a stepper motor control apparatus to move the tip in a defined pattern. Each of the coils can be separately connected to the ultrasonic signal generator.

In another embodiment, each of the coils is connected to a separate ultrasonic signal generator.

In yet another embodiment, at least one coil can have a longitudinal axis parallel to a longitudinal axis of the well and extending substantially from a proximal end to a distal end of the well. At least one coil can be disposed within a wall of the handpiece between the well and an outer surface of the handpiece.

In another embodiment, a longitudinal axis of the at least one coil can be transverse to a longitudinal axis of the well. A friction fit between an outer surface of the magnetic rod and an inner surface of the well can be provided as a fulcrum to vibratably retain the magnetic rod within the handpiece. An O-ring can be provided as a fulcrum to vibratably retain the magnetic rod within the handpiece.

In yet another embodiment, a positioning tab and a corresponding positioning notch can be formed between the outer surface of the magnetic rod and an inner surface of the well to restrict relative rotation therebetween. In an embodiment, a sealing member forms a fluid-tight seal between the outer surface of the magnetic rod and the inner surface of the well.

In another embodiment, a source of motive fluid can be in communication with an aperture in the tip. A channel in the magnetic rod can be in communication with the aperture in the tip and in communication with a fluid supply channel in the handpiece.

In yet another embodiment, a gripping element can be disposed as a fulcrum between the proximal and distal ends of the magnetic rod. The tip can be removably attached to the distal end of the magnetic rod. A metallic element can be disposed within the at least one coil along a longitudinal axis. The magnetic rod can include a ferromagnetic material. The tip can be a dental or surgical tip.

In another embodiment, a method of vibrating a tip of an ultrasonic tool can include affixing the tip to a magnetic rod, positioning the magnetic rod on a fulcrum disposed between the tip and a plurality of electromagnetic coils contained within a handpiece, and controllably energizing at least one of the electromagnetic coils to vibrate the magnetic rod and the tip.

In yet another embodiment, a method of vibrating a tip of an ultrasonic tool can include vibratably retaining a magnetic rod within a well of a handpiece of the ultrasonic tool, wherein the tip is adjacent an entry to the well and is attached to an end of the magnetic rod, connecting an ultrasonic signal generator to an energy source and to a plurality of electromagnetic coils disposed within the handpiece to provide an electromagnetic field, and varying the energy to at least one of the electromagnetic coils to change the electromagnetic field with the ultrasonic signal generator to reciprocate the magnetic rod and thereby vibrate the tip.

In another embodiment, the step of varying the energy further comprises varying the energy with a stepper motor control apparatus. A longitudinal axis of each of the electromagnetic coils can be parallel to a longitudinal axis of the well. A longitudinal axis of each of the electromagnetic coils can be transverse to a longitudinal axis of the well.

In yet another embodiment, the method of vibrating a tip of an ultrasonic tool can include applying the tip to impact or penetrate a substrate. The method can include applying the tip to clean, cut, polish, abrade or massage a dental surface.

In another embodiment, an ultrasonic tool can include a handpiece, an insert retained in the handpiece comprising a proximal movable pin transducer rigidly carrying a distal working tip, and ultrasonic drive means comprising coils in the handpiece to generate an electromagnetic field of varying anisotropy adjacent a pin of the moveable pin transducer for repetitively moving the pin in response to an ultrasonic drive signal and thereby vibrating the working tip in a defined pattern.

DETAILED DESCRIPTION

Figure 1:
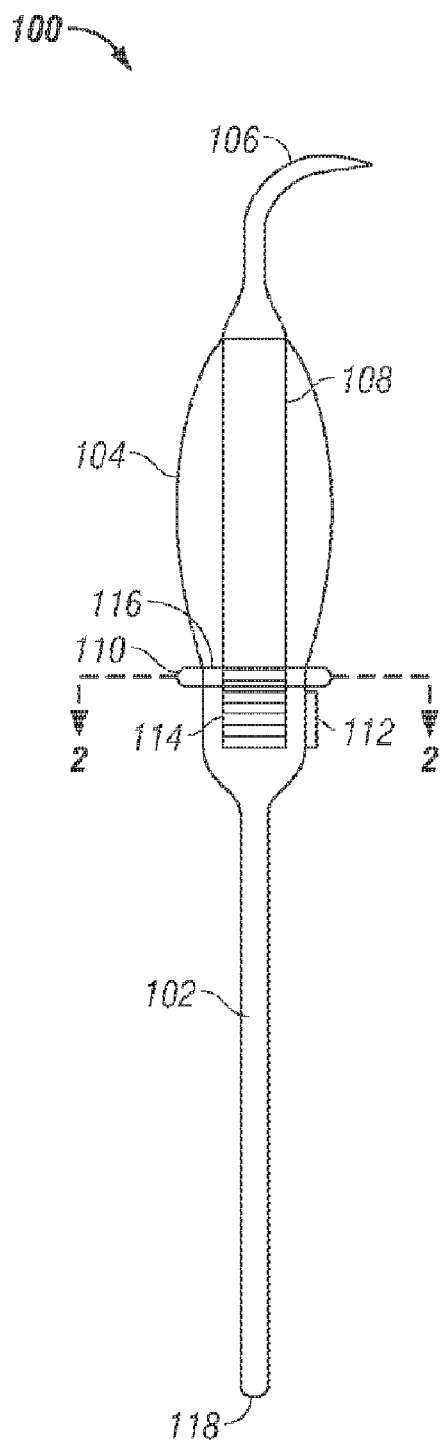
FIG. 1 is a side schematic view of a moveable pin transducer of an ultrasonic tool, according to one embodiment of the invention.

With reference to the figures wherein like reference numerals are used to refer to like parts, FIG. 1 shows a moveable pin transducer (MPT) 100 of an ultrasonic tool, according to one embodiment of the invention. The MPT 100 includes a magnetic rod 102 and a tip 106. Tip 106 can be a dental or surgical tip as is know in the art. The tip 106 is generally manufactured from a tubing piece of the appropriate inside and outside diameters which is bent and molded into the desired shape and then hardened and polished. A stainless steel, such as 420 or 440 grade, is generally suitable for this purpose, but, depending on the function or purpose of the tip 106, it can also be made from titanium or other materials, and can optionally be coated with an abrasive material such as diamond. The tip 106 can be a universal tip, a left tip or a right tip, have flattened sides and a spooned end, or can be a surgical blade, or any other element suitable for ultrasonic use. The tip can have an aperture connected to a channel (not shown) to allow a motive fluid to flow therethrough. Although the invention is illustrated for the purpose of clarity with reference to an ultrasonic dental tool, it will be readily appreciated by those skilled in the art that the tool of the present invention can be configured within the scope of the present invention for other purposes such as surgical tools, sculpting tools, and the like.

Tip 106 is rigidly attached to a connecting body 108, which is engaged in a threaded female connector 114 formed in the magnetic rod 102. Conversely, the threaded female connector 114 can be formed in the connecting body 108 and the threaded male connector can be formed on the magnetic rod 102. The connecting body 108 is disposed within a gripping element 104. The gripping element 104 can be any shape or style as known in the art. The connecting body 108 itself can be a gripping element or integral with the gripping element 104. The tip 106 can be permanently or removably attached to magnetic rod 102 and/or connecting body 108 by any means known in the art. The optional gripping element 104 can be disposed directly over the magnetic rod 102, to eliminate use of the connecting body 108, with the tip 106 directly attached to, or even formed integral with, the magnetic rod 102.

The magnetic rod 102 can be any style, size, or shape known in the art. The magnetic rod 102 can be cylindrical. The magnetic rod 102 can consist of two or more adjacent rods operatively connected (not shown), e.g., a tuning fork. The magnetic rod 102 can taper from a larger distal end 116 to a smaller proximal end 118 (as shown), or vice versa. As used herein the term "magnetic" includes any type of magnetic or magnetizable material, including ferromagnetic, diamagnetic and/or paramagnetic materials, that can be used in a rigid rod or part thereof to move the rod by attraction to and/or repulsion from the electromagnetic field generated in the handpiece. The magnetic rod 102 can be formed, at least partially, from any suitably magnetic ferromagnetic, diamagnetic, and/or paramagnetic material that exhibits or can be made to exhibit attraction and/or repulsion to a magnetic or electromagnetic field. As representative magnetizable materials there may be mentioned, for example, iron, nickel, cobalt, ceramic ferrite, magnetic stainless steel alloy, and/or any alloy that exhibits extremely high magnetic permeability. As representative magnet materials, there may be mentioned neodymium or NdFeB (neodymium, iron, and boron) magnets, AlNiCo (aluminum, nickel, and cobalt) magnets, samarium or SmCo (samarium and cobalt) magnets, ferrite magnets, ceramic magnets, and/or any rare earth magnets (for example, those from Lanthanides portion of the Periodic Table of Elements).

The magnetic rod 102 can be a composite of magnetic and non-magnetic materials, for example, titanium or aluminum with a section or coating of magnetic material. The magnetic rod 102 can be a polymer coated or interspersed with at least one magnetic powder, for example, a polymer matrix supporting magnetic powder that can be injection or otherwise molded. The magnetic rod 102, or a portion thereof, can be non-circular, e.g. ovate (see FIG. 2B), square, rectangular, hexagonal, or other polygonal, with respect to a cross-section that is transverse to the longitudinal axis of the magnetic rod 102, and is not limited to the circular cross-section shown by the dotted line in FIG. 2A.

The magnetic rod 102 can have a channel (not shown) therethrough. The channel can be in fluid communication with an aperture (not shown) in the tip to provide a motive fluid to an area ultrasonically acted upon, for example, water and/or air can be used during a tooth scaling procedure.

Figure 2B:
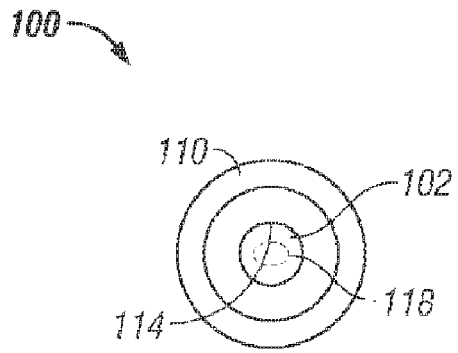
FIG. 2B is a cross-sectional schematic view of a second embodiment of the moveable pin transducer of FIG. 1 as seen along the lines 2-2, wherein the narrow portion of the tapered magnetic rod is ovate.
Figure 3:
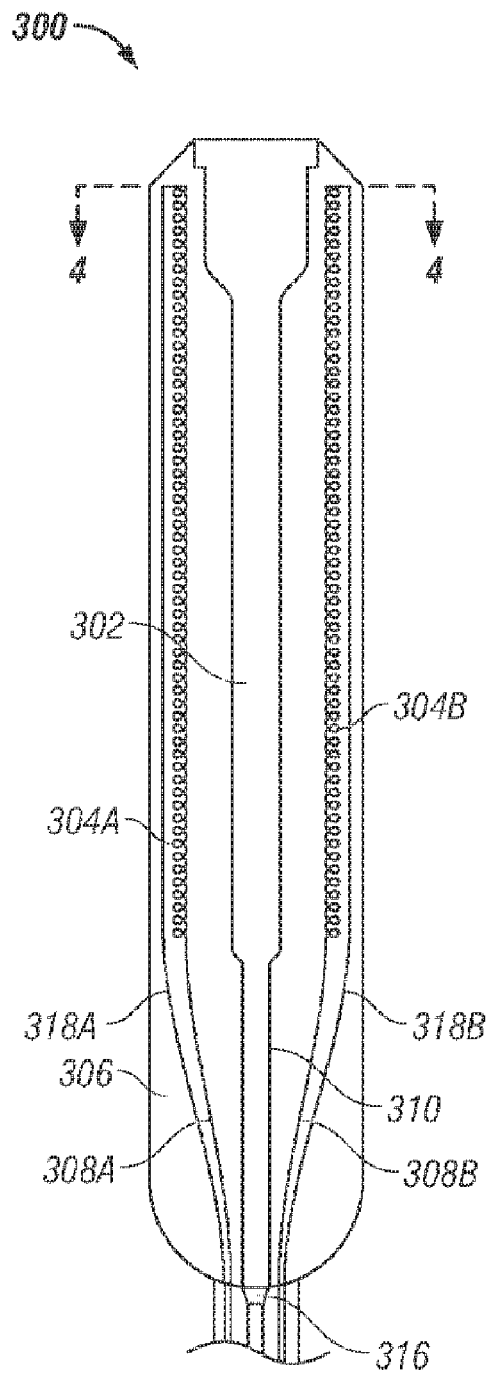
FIG. 3 is a side schematic view of a handpiece of an ultrasonic tool containing a plurality of electromagnetic coils disposed adjacent a well, according to one embodiment of the invention.
Figure 4A:
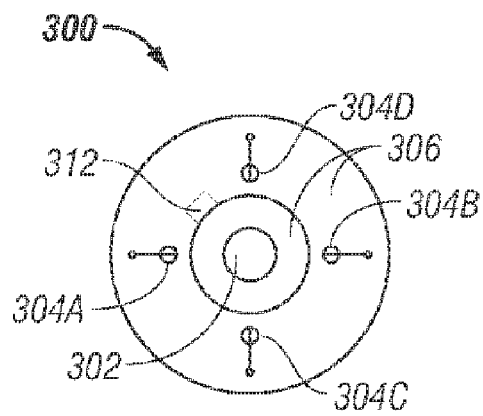
FIG. 4A is a cross-sectional schematic view of the handpiece of FIG. 3 as seen along the lines 4-4, wherein the circumference of the narrowly tapered portion of the well is circular.
Figure 4B:
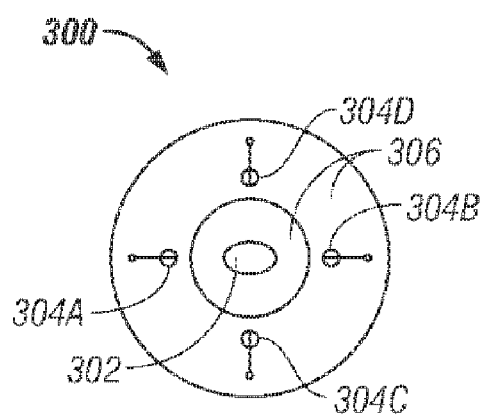
FIG. 4B is a cross-sectional schematic view of a second embodiment of the handpiece of FIG. 3 as seen along the lines 4-4, wherein the circumference of the narrowly tapered portion of the well is ovate.
Figure 5:
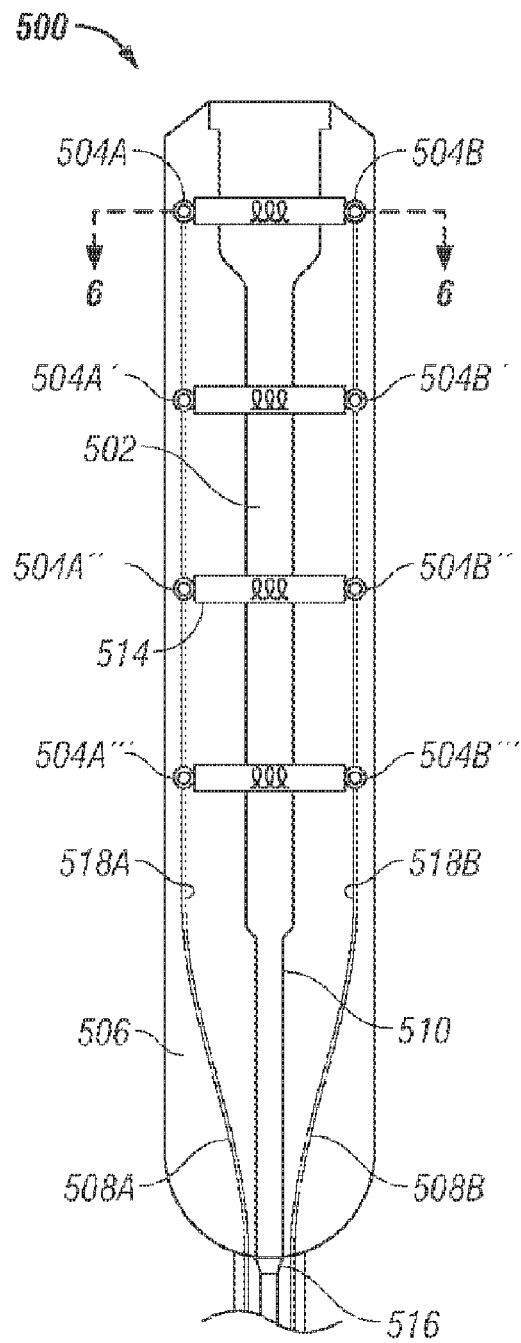
FIG. 5 is a side schematic view of a handpiece of an ultrasonic tool containing a plurality of electromagnetic coils disposed adjacent a well, according to one embodiment of the invention.
Figure 8A:
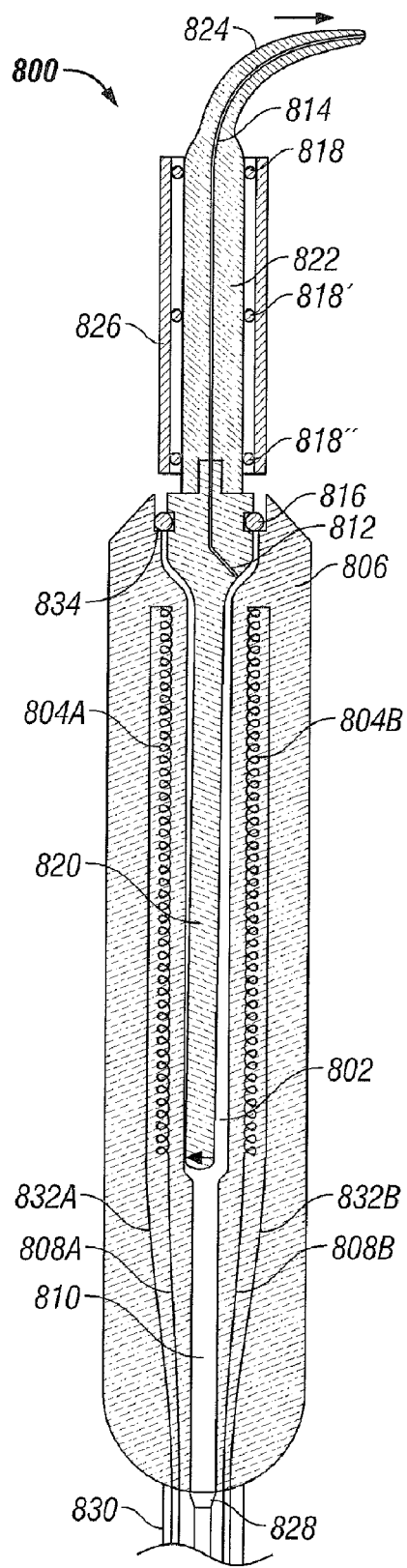
FIG. 8A is a cross-sectional view of an ultrasonic tool wherein the tip of the moveable pin transducer is displaced to the right by energizing one of the handpiece electromagnetic coils, according to one embodiment of the invention.
Figure 8B:
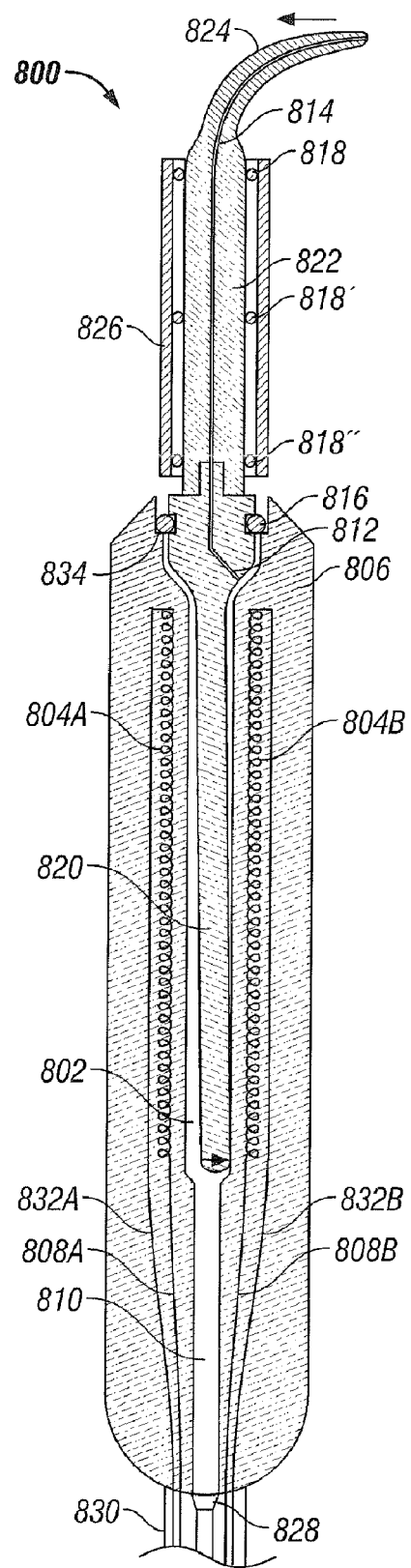
FIG. 8B is a cross-sectional view of the ultrasonic tool of FIG. 8A, wherein the tip of the moveable pin transducer is displaced to the left by energizing the opposite handpiece electromagnetic coil.

Further, an optional positioning tab 112 can be located on the outer surface of the magnetic rod 102 or other portion of the MPT 100, with the positioning tab 112 disposed in a corresponding positioning notch (312 in FIG. 4A) in a handpiece when the MPT 100 is inserted into a handpiece (300 in FIG. 3, 500 in FIG. 5, 806 in FIGS. 8A-8B). The use of a positioning tab 112 can be eliminated if the magnetic rod 102 and the well (302 in FIG. 3, 502 in FIG. 5, 802 in FIGS. 8A-8B) are respectively shaped at an adjacent portion to restrict rotation therebetween, e.g. the cross-section of the narrow portion (dotted line 118 in FIG. 2B) of tapered magnetic rod 102 and the well (302 in FIG. 4B, 502 in FIG. 6B) each being ovate and the gap therebetween sufficiently tight to restrict rotation, but allow ultrasonic vibration.

To permit movement or vibration between a magnetic rod 102 or other portion of the MPT 100 and a handpiece (300 in FIG. 3, 500 in FIG. 5, 806 in FIGS. 8A-8B), an O-ring is provided. However, any element, or plurality of elements, capable of serving as a fulcrum can be utilized. In a preferred embodiment, said fulcrum is disposed between the proximal and distal ends of the MPT and coupled to a handpiece at a distal end of the well. The O-ring 110 in FIG. 1 is shown disposed between the magnetic rod 102 and the gripping element 104, however it can be disposed anywhere between an MPT 100 and a handpiece (300 in FIG. 3, 500 in FIG. 5, 806 in FIGS. 8A-8B) to allow vibration therebetween. The O-ring 110 can fluidicly seal the moveable MPT 100 to the well (302 in FIG. 3, 502 in FIG. 5, 802 in FIGS. 8A-8B), but is not a requirement. The O-ring 110 can be formed integral to the gripping element 104 to create a unitary gripping and sealing member. Any sealing member known in the art can optionally be used to seal a portion of the MPT 100 to the well.

Figure 2A:
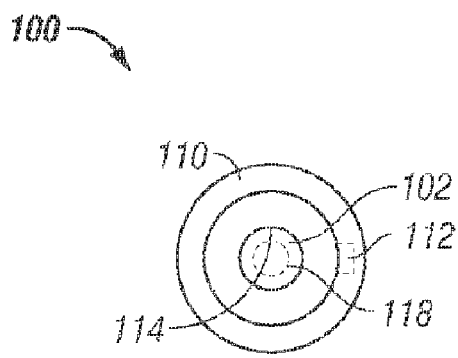
FIG. 2A is a cross-sectional schematic view of the moveable pin transducer of FIG. 1 as seen along the lines 2-2, wherein the narrow portion of the tapered magnetic rod is circular.

FIG. 2A is a cross-sectional schematic view of the MPT 100 as seen along the lines 2-2. Positioning notch 112, shown as a dotted line, is below O-ring 110, but can be formed above the O-ring, on the connecting body 108 for example. Positioning notch 112 can prevent rotation between the MPT 100 and a handpiece (300 in FIG. 3, 500 in FIG. 5), if so desired. The narrow, or proximal, portion of the tapered magnetic rod 102 can have a circular cross-section, as shown by dotted line 118. The proximal end 118 of the magnetic rod can have a convex surface as shown or be flat.

FIG. 2B is a cross-sectional schematic view of an alternative embodiment of the MPT 100 as seen along the lines 2-2. The narrow, or proximal, portion of the tapered magnetic rod 102 can have an oval cross-section, as shown by dotted line 118 in FIG. 2B. Similarly, the entire magnetic rod 102 or MPT 100, can be ovate or any polygonal shape. For example, the non-tapered distal end 116 of the magnetic rod 102 can have an ovate cross-section (not shown).

In use, the MPT 100 is disposed, at least partially, within a handpiece (300 in FIG. 3, 500 in FIG. 5, 806 in FIGS. 8A-8B) of the ultrasonic tool, as illustrated in FIGS. 8A-8B. FIG. 3 is a schematic cross-section of one embodiment of a handpiece 300. The magnetic rod 102 of an MPT 100, when disposed within the well 302 of a handpiece 300, is subjected to the magnetic forces created by the flow of electrical current through electromagnetic coils (304A-304D). The entire magnetic rod 102 of an MPT 100 can be disposed within the well 302. The amount and/or polarity of electrical current, and thus the geometry of the electromagnetic field produced, can be manipulated, for example, by alternating the current at a high rate or frequency to cause the magnetic rod 102, and the attached tip 106, to vibrate. An ultrasonic signal generator, for example, a stepper motor control apparatus as discussed below in connection with FIGS. 13-14, can be used to control the electromagnetic forces, and thus control the imparted vibratory forces. During use, a user can hold the ultrasonic tool on the handpiece 300 and/or the MPT 100, for example, if equipped with a gripping element 104. The tip 106, which extends from the entry of the well 302, can then be used in an ultrasonic procedure. For example, a user can apply the tip 106 to impact or penetrate a substrate or clean, cut, polish, abrade, or massage a dental surface. An MPT can be interchangeable for use with multiple handpieces, or vice versa.

Coils (304A-304D), or inductors, can be formed from any type of material suitable for creating an electromagnetic coil and can have any number of turns desired. A coil (304A-304D) can include a metallic member (not shown), for example, iron, which can be disposed coaxial to the longitudinal axis of the wound coil (304A-304D). Depending on the orientation of the coils ([304A-304D] in FIGS. 3 and 4A-4B; [504A-504A''', 504B-504B''', 504C-504C''', 504D-504D'''] in FIGS. 5 and 6A-6B) and/or magnetic rod 102, linear, axial, and/or rotary motion can be imparted therebetween. Although the coils (304A-304D) are shown extending substantially the entire depth of the well 302, the invention is not so limited.

The four coils (304A-304D), shown more clearly in FIG. 4A, are illustrated with their respective longitudinal axes parallel to the longitudinal axis of the well 302. FIG. 4B illustrates an alternative embodiment of the handpiece 300 wherein the well 302 has an ovate circumference, which can permit use with an ovate magnetic rod 102, for example, as shown in FIG. 2B. The well 302 can similarly be any polygonal shape, as disclosed above.

By arranging the four coils (304A-304D) in a longitudinal manner, the electrical current can be controlled in each coil (304A-304D) such that a set of coils (304A-304D) disposed approximately 180° apart have opposite electromagnetic fields which can be alternated to create a vibration effect, as illustrated in FIGS. 8A-8B. Four coils (304A-304D) are shown in FIGS. 3 and 4A-4B by way of example only. Any number of coils (304A-304D) can be utilized, preferably with the ultrasonic signal generator and/or ultrasonic drive signal modified accordingly. Coils can be disposed in any configuration, and are not limited to the 90° circumferential spacing show in FIGS. 4A-4B and 6A-6B. A coil (304A-304D) can be mounted in any orientation within the handpiece 300 and/or well 302 without departing from the spirit of the intention. By controlling the direction of flow, duration, and/or quantity of electrical current, the electromagnetic fields in each coil (304A-304D) can be precisely manipulated. Such manipulation of magnetic fields is well known by one of ordinary skill in the art.

By utilizing electromagnetic fields to control the vibration or other repetitive movement of the MPT 100, an operator has precise control of the direction of movement and/or the frequency of vibration. This allows utilization of high frequency vibrations, such as 80 kHz, when delicate low power work is being performed, for example. It also allows the same ultrasonic tool to be adjusted to a lower frequency, such as 20 kHz, when desired for performing less delicate work requiring higher power, for example. An ultrasonic tool utilizing an MPT 100 and handpiece (300, 500, 806) can provide high precision frequency control over a wide range of frequencies, making it superior to traditional transducer-based tools which can be limited to a narrow range of resonant frequencies. In addition to manipulating the electrical current, the length and/or mass of the magnetic rod 102, as well as the dimensions of the well 302, can be optimized to permit the MPT 100 of the ultrasonic tool to vibrate at a desired frequency.

The coils (304A-304D) can be formed within the handpiece body 306 and/or disposed at least partially within the well 302. The handpiece body 306 can be any suitable material for housing electrical coils (304A-304D). The coils (304A-304D) can be formed into one type of material, for example, a heat resistant material, with that assembly disposed within a handpiece 300 formed of a second type of material, which can be less heat resistant. The well 302 can be lined with an elastomeric material to protect the MPT 100 from damage. Any portion of, or the entirety of, an MPT 100 and/or handpiece 300 can be autoclavable, if so desired. An electrical conductor (308A, 308B, 318A, 318B) providing current to the coils (304A-304D) can be any type known in the art. In a preferred embodiment, each longitudinal pole coil has two electrical conductors connected thereto. For example, electrical conductors 308A and 318A are connected to opposite ends of coil 304A. Either conductor (308A, 318A) connected to a coil 304A can function as the current, or ultrasonic drive signal, carrying conductor, with the other serving as a ground wire, for example. This flow of current can be reversed, so as the ground conductor becomes the hot conductor, and vice versa. Further, each coil can be connected to a common ground conductor (not shown), for example eliminating conductors (for example, 318A and 318B) and having one common conductor connecting the four coils (304A-304D). Handpiece 300 can include an outer covering or other type of shield to limit electromagnetic interference (EMI).

FIG. 3 further illustrates an optional fluid source supply channel, or port, 310 in the handpiece 300. The MPT 100 can have an aperture in its tip 106 in fluid communication with the fluid supply channel 310, for example, through a longitudinal channel (not shown) through the MPT 100. Fluid supply channel 310 provides fluid to the well 302 by connecting a source of motive fluid to the handpiece nipple 316. Further, independent of an MPT 100, namely the tip 106, allowing the flow of a motive fluid therethrough, the motive fluid, for example, water, supplied to the well 302 can cool the magnetic rod 102 of the MPT 100. A second fluid channel (not shown) can be in communication with the well 302 to allow the egress of fluid, for example, to permit fluid circulation through the well 302 to aid in the cooling process.

FIG. 4A is a cross-sectional view of the handpiece 300 as seen along the lines 4-4. A positioning notch 312 can be formed in the inner surface of the handpiece well 302. A respective positioning tab 112 of the MPT 100, when the MPT 100 is installed in the handpiece 300, can be disposed within the positioning notch 312, to impede relative rotation between the handpiece 300 and MPT 100. FIG. 4B illustrates an alternative embodiment of the handpiece 300 wherein the well 302 has an ovate circumference.

An MPT 100 can be vibratably retained within the handpiece 300 by a friction fit between a portion of an outer surface of the MPT 100, or magnetic rod 102 itself, and a portion of an inner surface of the well 302. A resilient member between a portion of an outer surface of the MPT 100, or magnetic rod 102 itself, and a portion of an inner surface of the well 302, can be added to aid in vibratably retaining the MPT 100 within the handpiece 300. An MPT 100 can be permanently, but vibratably, attached to the handpiece 300 or can be removable from the handpiece 300. For example, an O-ring 110 can removably retain the MPT 100 within the handpiece 300. As discussed above, the cross-section of the well 302 can be circular as shown in FIG. 4A. Further, the well 302, as shown in FIG. 4B, and MPT 100, as shown in FIG. 2B, can each be ovate to restrict relative rotation therebetween and thus no positioning tab 112 and respective notch 312 would be needed. Regardless of how the MPT 100 is vibratably retained within the handpiece 300, any type of sealing member between an outer surface of the MPT 100, or magnetic rod 102 itself, and handpiece 300, for example, the inner surface of the well, can be utilized. An optional O-ring shoulder at the distal end of the handpiece 300 can be included, for example, to restrict the proximal end 118 of the magnetic rod 102 of the MPT 100 from contacting the floor of the well 302.

The well 302 can be sized relative to the magnetic rod 102, for example, both can taper from a larger proximal end to a smaller distal end as shown, or vice versa. The gap between the inner wall of the well 302 and the magnetic rod 102 can be any size, and/or can be variable throughout, to allow vibration between the magnetic rod 102 and handpiece 300. Preferably the gap is 20 to 30 thousandths of an inch, for example, as measured when the longitudinal axis of the magnetic rod 102 is coaxial to the longitudinal axis of the well 302.

Figure 6A:
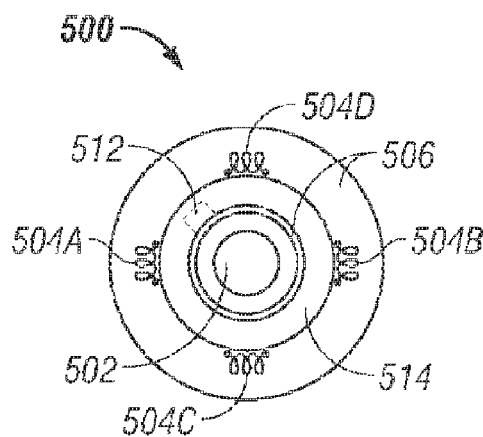
FIG. 6A is a cross-sectional schematic view of the handpiece of FIG. 5 as seen along the lines 6-6, wherein the circumference of the narrowly tapered portion of the well is circular.
Figure 6B:
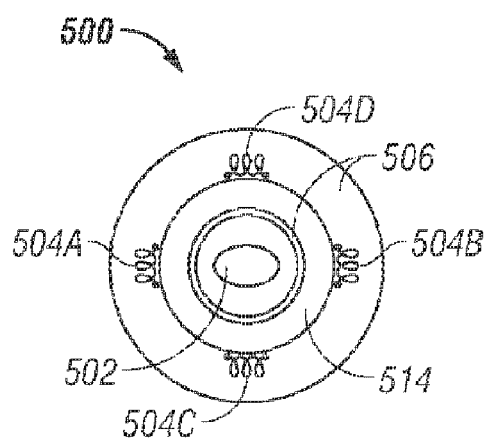
FIG. 6B is a cross-sectional schematic view of a second embodiment of the handpiece of FIG. 5 as seen along the lines 6-6, wherein the circumference of the narrowly tapered portion of the well is ovate.

Another embodiment of a handpiece 500 containing electromagnetic coils 504 arranged in a radial, or ring, configuration is shown in FIGS. 5 and 6A-6B. The handpiece 500 provides the same basic advantages of the handpiece 300 embodiment in FIGS. 3 and 4A-4B, but provides an alternate implementation. While the embodiment of FIG. 5 functions similarly to the embodiment of FIG. 3, it can require a different ultrasonic signal generator to controllably supply current, as the geometry of the coils, and thus the electromagnetic fields generated, can be dissimilar.

FIGS. 5 and 6A-6B illustrate electromagnetic coils (504A-504A''', 504B-504B''', 504C-504C''', 504D-504D''') disposed circumferentially around the well 502 of a handpiece 500. Although shown as being disposed within the handpiece on mounting rings 514, these are not required. The coils can be formed directly into the handpiece body 506 without the use of mounting rings 514. The electromagnetic coils (504A-504A''', 504B-504B''', 504C-504C''', 504D-504D''') can include a metallic member (not shown), for example, iron, which can be disposed coaxial to the longitudinal axis of the wound coil, to increase the strength of an electromagnetic field produced.

Although the coils (504A-504A''', 504B-504B''', 504C-504C''', 504D-504D''') shown in FIGS. 5 and 6A-6B have a longitudinal axis that is tangential to the outer circumference of the mounting ring 514 and perpendicular to the longitudinal axis of the well 502, a coil can be rotated 90° from this position, such that the longitudinal axis of the coil is parallel to the longitudinal axis of the well 502. The use of a mounting ring 514 is optional and is referred to here for orientation purposes. Further, a coil (504A-504A''', 504B-504B''', 504C-504C''', 504D-504D''') can be disposed such that a longitudinal axis of the coil extends radially from the longitudinal axis of the well 502. Coils can be mounted in any orientation within the handpiece 500, for example, zigzag, without departing from the spirit of the intention. A single handpiece 500 can include coils mounted in differing orientations to create both lateral and radial movement of an MPT 100.

Four sets of optional mounting rings 514 are shown, however any number of mounting rings can be used. Although each mounting ring 514 is shown with four coils (for example, 504A, 504B, 504C, 504D) mounted thereto, one or more coils, in any orientation and/or configuration, can be utilized, as is further shown in FIGS. 9-12. As noted above, the use of a mounting ring 514 is optional, and the coils can be mounted in the same orientation and configuration shown by disposing the coils (504A-504A''', 504B-504B''', 504C-504C''', 504D-504D''') directly within the handpiece body 506.

To power the coils, a plurality of electrical conductors (508A, 508B) can be conductively attached to the coils. An electrical conductor 508A can extend to each set of longitudinally adjacent coils (for example, 504A-504A'''), as shown or to each set of circumferentially adjacent coils mounted on a single ring 514 (for example, 504A-504D). Preferably, a conductor 508A is connected to an end of each coil (for example, coils 504A-504A'''), with the other end of each coil connected to a second conductor (shown more clearly in FIGS. 6A-6B). Either of these conductors can be used as a ground or power conductor. Similarly, as each of the sixteen coils (504A-504A''', 504B-504B''', 504C-504C''', 504D-504D''') shown typically has a first and a second connection at opposing ends, as more clearly illustrated in FIGS. 6A-6B, to allow electrical current to flow therethrough, two electrical conductors can be connected to each individual coil. The coils can be connected a common ground conductor, if so desired to reduce the number of electrical conductors disposed in the handpiece 500. The coils (504A-504A''', 504B-504B''', 504C-504C''', 504D-504D''') can be wired in series, parallel, or any combination thereof, without departing from the spirit of the invention.

Figures 7A, 7B:
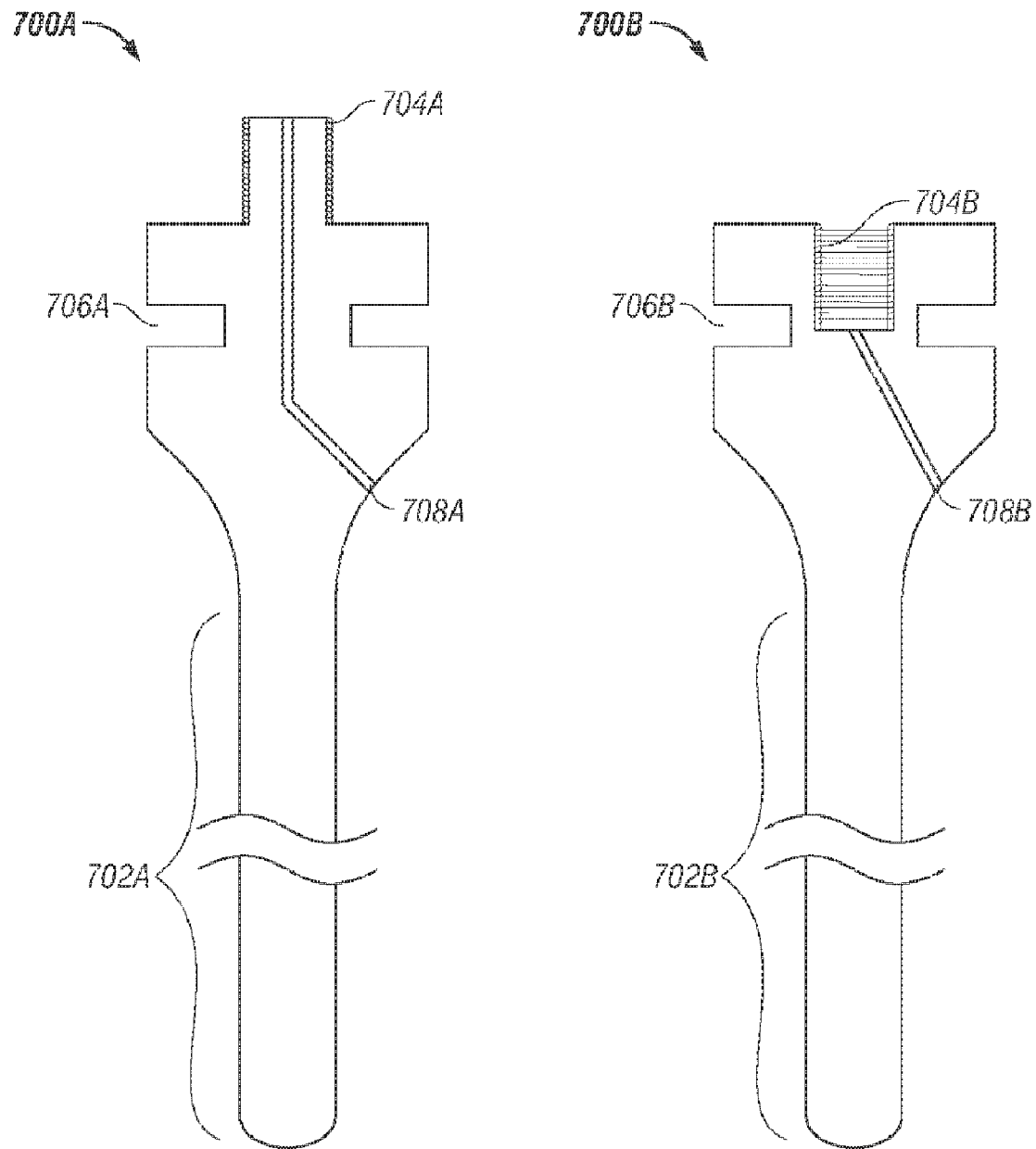
FIG. 7A is a side schematic view of a magnetic rod of a moveable pin transducer of an ultrasonic tool, according to another embodiment of the invention.
FIG. 7B is a side schematic view of a magnetic rod of a moveable pin transducer of an ultrasonic tool, according to a second embodiment of the invention.

An optional fluid supply channel 510 in the handpiece 500 can supply a motive fluid to the well 502 for cooling. The fluid supply channel 510 can also provide a channel in the MPT, as shown in FIGS. 7A-7B, with fluid to cool and/or clean the tip and/or surface being ultrasonically acted on. The handpiece nipple 516 can connect the fluid supply channel 510 to a source of motive fluid. As shown in FIG. 6A, a positioning notch 512 can be formed in the wall of the handpiece well 502, for interaction with a respective positioning tab 112, if present, on an MPT 100. FIG. 6B illustrates an alternative embodiment of the handpiece 500 wherein the well 502 has an ovate circumference, which can permit use with an ovate magnetic rod 102, for example, as shown in FIG. 2B. The well 502 can similarly be any polygonal shape, as disclosed above.

The handpieces (300, 500, 806) are for illustrative purposes only, any handpiece containing coils capable of generating an electromagnetic field and/or vibratably retaining a magnetic rod can be used. The magnetic rod 102 of a movable pin transducer (MPT) 100, as shown in FIGS. 1 and 2A-2B, can be attached to any ultrasonic tip 106 to permit use thereof.

FIG. 7A shows another embodiment of the magnetic rod 700A of a moveable pin transducer (MPT). The magnetic rod 700A in this embodiment is one piece and includes a narrowly tapered magnetic rod portion 702A or pin. An entire MPT can be made of the same material or multiple materials can be used, as desired. The tapered magnetic rod portion 702A can be any diameter, length, or taper. The tapered magnetic rod portion 702A can be an annular ring of magnetic material disposed over a portion of the magnetic rod 700A which can be any material. However, a magnetic rod 700A, can be a simple cylinder.

A threaded male connector 704A is formed on the distal end of the magnetic rod 700A. The threaded male connector 704A can connect to any tip and/or gripping element for ultrasonic use. An optional fluid channel 708A extends within the magnetic rod 700A. When the magnetic rod 700A is inserted into a handpiece, for example, handpiece 300 of FIG. 3, an O-ring (not shown) disposed within O-ring groove 706A seals and vibratably retains the magnetic rod 700A within the well 302. Multiple grooves 706A, and O-rings, can be used without departing from the spirit of this invention.

Further, the well (302, 502, 802) of any handpiece can be respectively configured to allow the magnetic rod 700A of an MPT to be disposed within the well. For example, a well can be of a larger size at a distal end to house the larger distal end of the magnetic rod 700A in FIG. 7A, with the well narrowing to follow the taper of the magnetic rod 700A to allow movement therebetween. In the embodiment of FIG. 7A, an O-ring (not shown) can allow the magnetic rod 700A of the MPT to be vibratably retained within a handpiece (300, 500, 806) and/or seal the magnetic rod 700A within the well of a handpiece. Thus, to allow vibration, a handpiece and a magnetic rod 700A preferably allow for a gap therebetween.

Referring again to FIG. 3, a handpiece 300 with an optional fluid supply channel 310 can thus communicate with a fluid channel 708A in the magnetic rod 700A, with an O-ring sealing the magnetic rod 700A to the handpiece 300 to create a chamber therebetween. The fluid channel 708A can be in fluidic communication with any tip attached to the threaded male connector 704A. Tips containing apertures for use with fluids are known by those of ordinary skill in the art. An MPT and/or the magnetic rod 700A of an MPT can be any length, diameter, or shape. The magnetic rod 700A itself can function as an MPT, for example, by forming a grip and/or tip on a distal end of the magnetic rod 700A.

FIG. 7B shows another embodiment of a magnetic rod 700B, with a threaded female connector 704B formed in the distal end of the rod. An optional fluid channel 708B is in communication with the threaded female connector 704B. A fluid channel 708B can have any path through the magnetic rod 700B, for example, the fluid channel can extend along a longitudinal axis of the rod 700B (not shown). Further, a source of motive fluid can be in fluidic communication directly with a tip without the source extending through the MPT, magnetic rod 700B, and/or handpiece. A tapered magnetic rod portion 702B is provided and can be threadably connected (not shown) to the distal portion of the magnetic rod 700B, which is not necessarily magnetic and can be aluminum, titanium or other material, as discussed above. A positioning tab (not shown) can be added to any magnetic rod or other portion of an MPT, for use with a positing notch (312, 512) in a handpiece.

To impart ultrasonic vibration to an MPT, the magnetic rod portion (102, 700A, 700B, 820) is inserted at least partially into the well of a handpiece containing electromagnetic coils. Said coils are then selectively energized to produce ultrasonic vibration. FIGS. 8A-8B illustrates how the selective powering of coils (804A, 804B) can impart movement to the tip 824 of an ultrasonic tool 800. FIG. 8A is cross-sectional view of an ultrasonic tool 800 consisting of a handpiece 806 and a moveable pin transducer (MPT) that includes a magnetic rod 820. The handpiece 806 includes two electromagnetic coils (804A, 804B) disposed therein. Although two coils are illustrated, a single coil or plurality of coils can be used without departing from the spirit of the invention. Three dimensional movements can be achieved by this invention, for example using the handpiece of FIGS. 3 and 4A-4B. Opposing ends of each electromagnetic coil (804A, 804B) are connected to two electrical conductors (808A, 832A and 808B, 832B). The handpiece 806 can be attached to an optional cable or sheath 830 for encasing the electrical conductors (808A, 832A and 808B, 832B) and/or a fluid supply line that connects to the handpiece nipple 828. The handpiece nipple 828 is in fluid communication with the fluid supply channel 810, to provide fluid to the handpiece well 802.

The MPT portion of the ultrasonic tool 800 includes a magnetic rod 820, shown disposed within the well 802 of the handpiece 806. The MPT is shown vibratably retained in the handpiece by O-ring 816, but any fulcrum means can be utilized. An optional O-ring shoulder 834 can be formed in the entry to the well 802 to restrict longitudinal movement between the handpiece and the MPT. The magnetic rod 820 is threadably connected to a connecting body 822, which has a tip 824 on a distal end thereof. Tip 824 can be threadably attached (not shown) to the connecting body 822. Gripping element 826 is disposed on the connecting body 822 by three O-rings (818, 818', 818"), however any number of O-rings, or other dampening devices, can be used. The outside of gripping element 826 can be coated with a resilient material to allow further dampening and/or user comfort.

In use, coil 804A is energized by supplying electrical current through one of the electrical conductors (808A, 832A), the other of the electrical conductors (808A, 832A) serving as a ground. The resultant electromagnetic field attracts the magnetic rod 820. As the O-ring 816 serves as a fulcrum vibratably supporting the MPT of the ultrasonic tool 800, the proximal portion of the magnetic rod 820 is displaced within the well 802 towards the coil 804A while the tip 824 of the MPT is displaced in the opposite direction.

FIG. 8B illustrates the ultrasonic tool 800 in a second position. The coil 804B is conductively connected at opposing ends to a pair of electrical conductors (808B, 832B), with one of the electrical conductors (808B, 832B) supplying current and the other of the electrical conductors (808B, 832B) serving as a ground. Here, the second coil 804B has been energized and the first coil 804A has either been deactivated, or the strength of the electromagnetic field of coil 804B is stronger than the electromagnetic field of coil 804A. Resultantly, the proximal portion of the magnetic rod 820 is displaced within the well 802 towards coil 804B while the tip 824 of the MPT is displaced in the opposite direction due to the fulcrum formed by O-ring 816. Rapid selective powering and/or de-powering of the coils (804A, 804B) to displace the magnetic rod 820 can enable the attached tip 824 to vibrate at ultrasonic frequencies. Although FIGS. 8A-8B illustrate right and left motion of the tip 824 relative to the viewed orientation, any direction of vibration can be imparted, as discussed above, for example, by disposing the tip 824 at a different orientation, for example, rotating 90° from the illustrated position. Further, the vibratory geometric path of the tip can be varied by altering the position and/or number of coils (804A, 804B), for example.

Returning again to FIG. 8A, if one coil, for example, 804A, is energized, any unpowered coil, for example, 804B, can be utilized as a feedback or sensor coil due to the current produced in the unpowered coil by the electromagnetic field. Using unpowered coils as sensors can enable a user to monitor the electromagnetic field and/or allow automatic adjustment of the electromagnetic field when coupled with an ultrasonic signal generator. Further, separate sensors and/or sensor coils can be added without departing from the spirit of the invention.

By utilizing the electromagnetic coils (804A, 804B) as sensors, or using separate embedded sensors (such as hall effect devices) within the handpiece 806, to detect the position, speed, and/or magnetic characteristics of the MPT at precise intervals, an ultrasonic signal generator can automatically maintain the desired vibration pattern and/or strength, based upon a user's preset or ongoing needs of the tool(s). Design techniques for this type of ultrasonic signal (or pulse) generator are known to those skilled in the art.

The handpiece 806 of FIGS. 8A-8B also contain a fluid handpiece nipple 828 connected to fluid supply channel 810, to provide fluid to the handpiece well 802. The fluid in the handpiece well 802 can be used to cool the handpiece well 802 and/or magnetic rod 820, which can produce heat when vibrated at ultrasonic frequencies. An optional channel 812 in the magnetic rod 820 can be in fluidic communication with a respective channel 814 extending through the connecting body 822 to an aperture in the tip 824. Thus, any fluid supplied to the well 802, at a sufficient pressure, can flow through the channels (812, 814) and be discharged from the aperture in the tip 824.

Further, the gap shown between the magnetic rod 820 and the well 802 is exaggerated for illustrative purposes, and can be smaller, for example, 20 to 30 thousandths of an inch for use in vibrating in the 25 to 35 kHz frequency range. The gap can be design dependent such that the geometry of the magnetic rod 820 and/or well 802, and thus the gap therebetween, can be any desired configuration. The handpiece well 802 and/or magnetic rod 820 are not required to be cylindrical as shown, and can taper. For example, the well 802 can taper (not shown) from a larger proximal end to a smaller distal end to allow for the path of the magnetic rod 820 (e.g., the proximal end of the magnetic rod 820 can deflect or pivot further relative to the distal end of the magnetic rod 820 which is proximate the fulcrum 816). The dimensions of the magnetic rod 820 and/or the well 802 can be altered to achieve any desired configuration of a gap. Selection of an appropriate gap configuration can depend on the geometric pattern of movement and/or frequency or frequencies required to be generated by the ultrasonic tool for a specific application or use. For example, vibrating the magnetic rod 820 and attached tip 824 in a circular pattern of movement can require a smaller gap than when imparting an elliptical or side to side movement of the tip 824. Similarly, a higher frequency vibration can generally utilize a smaller gap than a lower frequency vibration. In the embodiment shown, a smaller gap generally results in a smaller amplitude of movement of the magnetic rod 820, and thus the levered tip 824. In addition to varying the dimensions of the gap, the length and/or mass of the magnetic rod 820 and the length from the fulcrum 816 to the tip 824 can be optimized to permit the MPT of the ultrasonic tool 800 to vibrate at a desired frequency and/or amplitude or produce a desired geometrical tip pattern.

Figure 9:
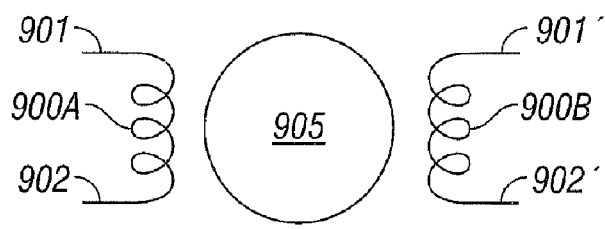
FIG. 9 is a schematic cross-sectional view of electromagnetic coils disposed adjacent to a magnetic rod of a moveable pin transducer, according to one embodiment of the invention.

As noted above, the electromagnetic coils can be disposed in any orientation, preferably with the electromagnetic field generated substantially acting on the magnetic rod of an MPT. A magnetic rod (102, 702A, 702B, 820), which can be annular or cylindrical, can then be excited into a state of vibration by the selective powering and de-powering and/or selective polarization of a plurality of coils. FIGS. 9-12 illustrate multiple configurations of electromagnetic coils (900A,900B; 1000A, 1000B; 1100A-1100D; 1200A-1200D) disposed adjacent to a portion of a magnetic rod (905, 1005, 1105, 1205) of a moveable pin transducer, however the invention is not limited to those configurations. Magnetic rod (905, 1005, 1105, 1205) is shown along a cross-section of a circular rod, however the rod can be ovate or any other shape as disclosed above. FIG. 9 is a schematic view of two coils (900A, 900B) disposed adjacent a magnetic rod 905 with 180° spacing. Electrical conductors can be connected to each end (901, 902; 901',902') of a coil (900A, 900B). Electrical current can flow from one end (901, 901') to another (902, 902') and/or be reversed. Each coil (900A, 900B can be individually controlled.

Figure 10:
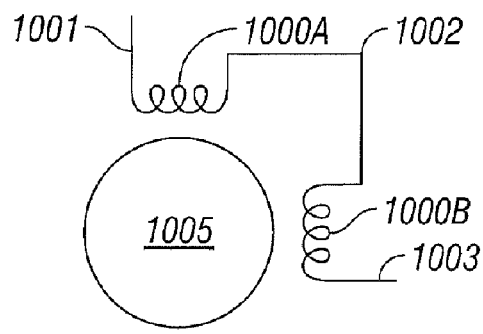
FIG. 10 is a schematic cross-sectional view of a second configuration of electromagnetic coils disposed adjacent to a magnetic rod of a moveable pin transducer, according to one embodiment of the invention.
Figure 11:
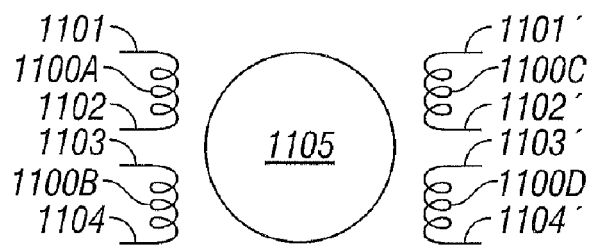
FIG. 11 is a schematic cross-sectional view of a third configuration of electromagnetic coils disposed adjacent to a magnetic rod of a moveable pin transducer, according to one embodiment of the invention.
Figure 12:
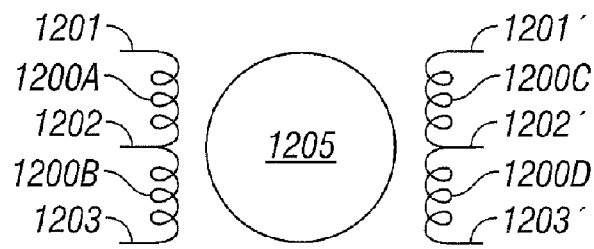
FIG. 12 is a schematic cross-sectional view of a fourth configuration of electromagnetic coils disposed adjacent to a magnetic rod of moveable pin transducer, according to one embodiment of the invention.

FIG. 10 is a schematic view of two coils (1000A, 1000B) disposed adjacent a magnetic rod 1005 with 90° spacing and wired in series. Similarly, the connection at 1002 can be connected to a common ground and coil ends (1001, 1003) each connected to a source of electrical current. FIG. 11 is a schematic view of four coils (1100A-1100D) disposed adjacent a magnetic rod 1105. Using coil 1100A for illustration, current can be supplied to either end (1101, 1102) of the coil and/or be alternated. FIG. 12 is a schematic view of four coils (1200A-1200D) disposed adjacent a magnetic rod 1205 and two sets of coils (1200A, 1200B; 1200C, 1200D) wired in series. The connection (1202,1202') can be used, for example, to add a current or other sensor. A Rogowski coil can be added to the handpiece to aid in sensing the current levels. Any of the coils can be used for their primary purpose, which is to generate an electromagnetic field, but a coil can also be used to measure the electric current and/or electromagnetic field as the MPT is being vibrated.

By precisely controlling the electromagnetic fields in the coils, the vibration frequency and/or pattern of the magnetic rod, and ultimately the tip of the MPT, can be precisely controlled. The pattern of movement of the magnetic rod, and attached tip, is governed by the shape of the tip and the vibratory pattern, frequency, and/or amplitude of the oscillations produced by the handpiece coils, which can be selectively powered by an ultrasonic signal generator. An ultrasonic generator can utilize stepper motor control software and/or programming to selectively power the electromagnetic handpiece coils to generate an electromagnetic field, as discussed below in reference to FIG. 13. The present invention allows virtually any pattern of tip movement to be selected, for example, side-to-side, top-to-bottom, in-out, or any combinations thereof that can produce circular, figure-8, and/or other geometric patterns. Prior art systems with limited control over the frequency of vibration have limited control over the tip oscillations. The oscillations are highly dependent on the tip geometry and the present invention can enable a user to compensate for various tip geometries.

Through the configuration of the coils, for example, as in FIGS. 3 and 4A-4B; 5 and 6A-6B; 8A-8B; and 9-12, and the ability to control the electrical current flow to each coil, and thus the electromagnetic field generated, the present ultrasonic tool can compensate for various tip geometries and/or any other factors that can affect the oscillations of the tip by varying the flow and/or polarity of electrical current to a specific coil. An operator can thus interchange tips and adjust the tool to maintain a desired oscillation pattern.

Preferably, the electromagnetic field, and thus the vibration of the MPT 100, is controlled by an ultrasonic signal generator. The ultrasonic signal generator controls the motion of the MPT, and any attached tip, by providing electrical current through the electrical conductors in a handpiece to energize the electromagnetic coils. The frequency, duration, voltage, power, and/or phase relationship of the electrical current to each coil of the handpiece determines how the magnetic rod, and any attached tip, reacts. For example, electrical current can be pulsed or alternated, to create vibration. The invention can be used with direct or alternating current.

An ultrasonic signal generator can be a pre-existing stepper motor control apparatus, as is know by one of ordinary skill in the art. By utilizing common control apparatus for stepper motors, an ultrasonic signal generator can be manufactured inexpensively. Common control apparatus include stepper motor control circuitry, translators, and/or drivers, as is known in the art.

Figure 13:
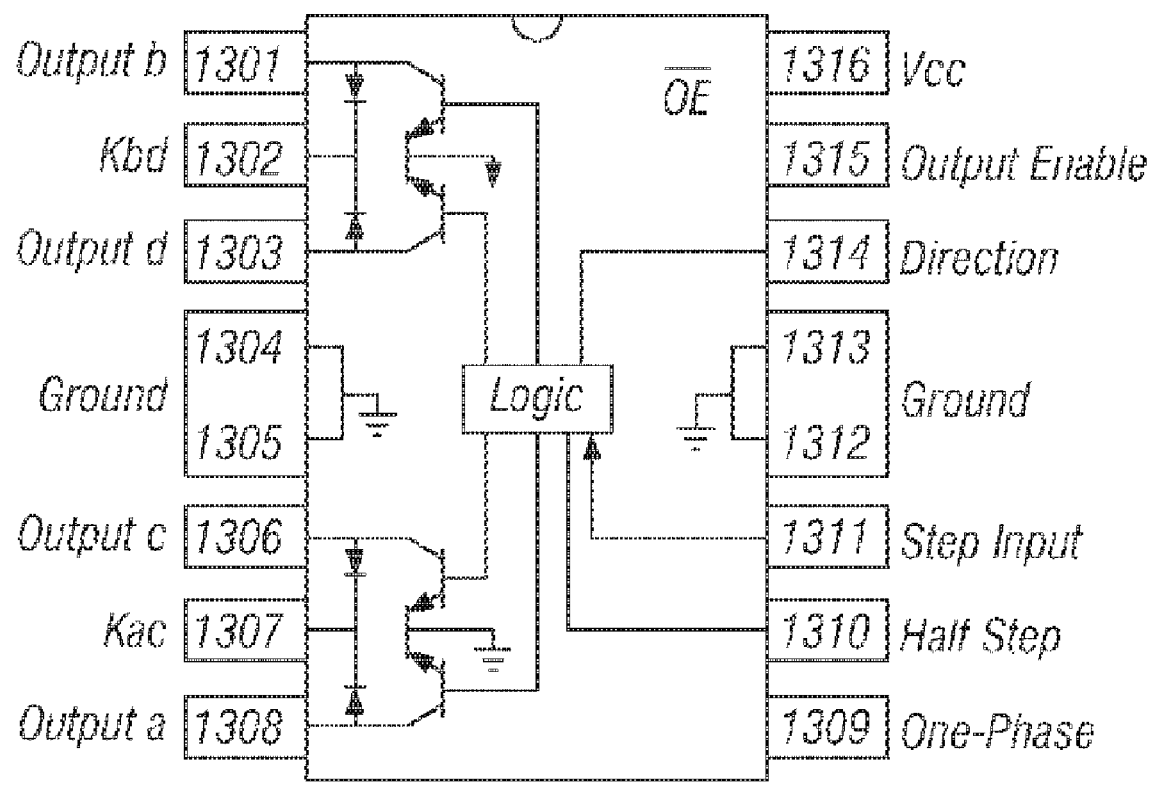
FIG. 13 is a schematic diagram of a stepper motor control driver to controllably energize electromagnetic coils, according to one embodiment of the invention.
Figure 14:
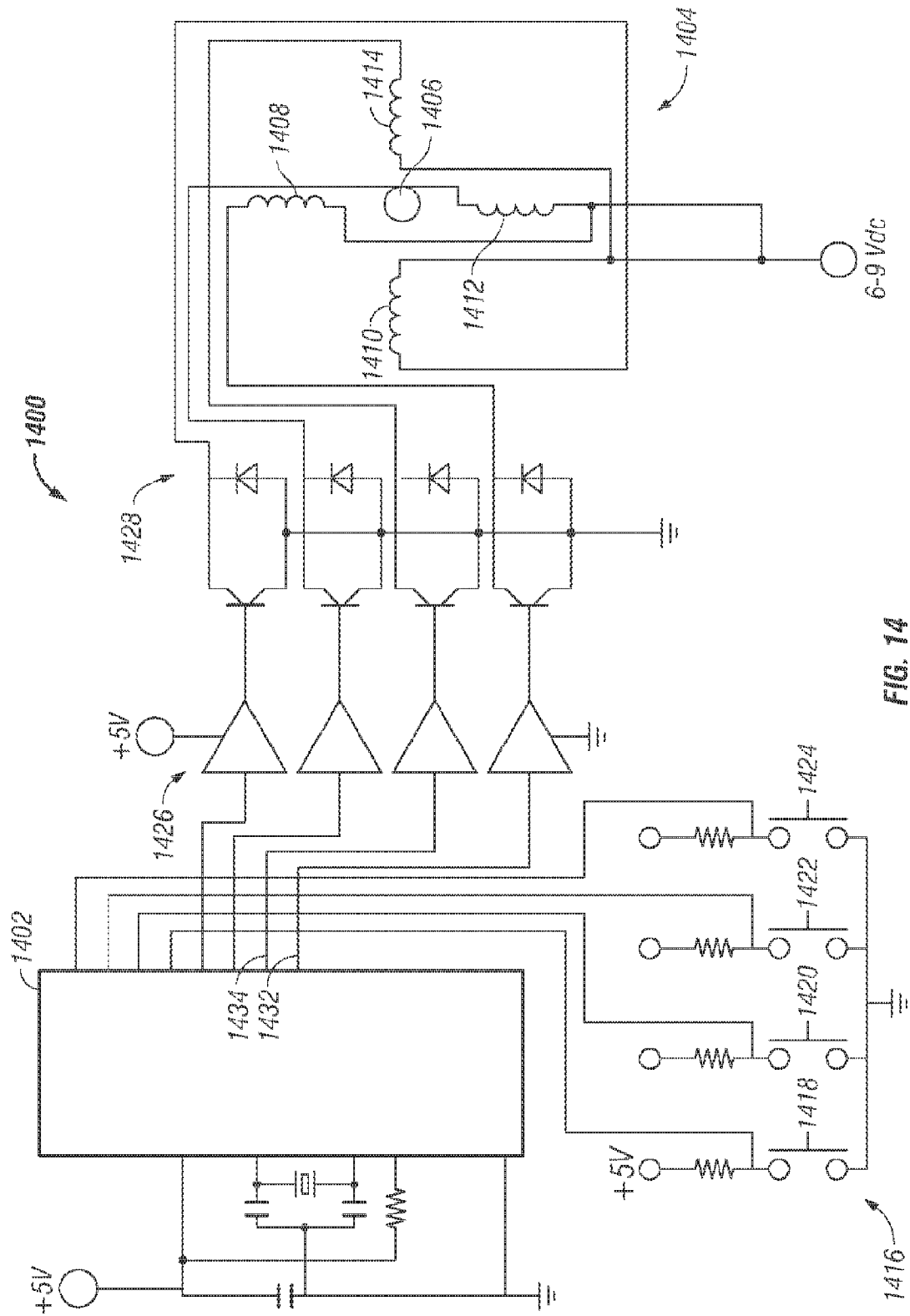
FIG. 14 is a schematic diagram of a stepper motor control circuit to controllably energize electromagnetic coils, according to one embodiment of the invention.

For example, a control apparatus that operates a stepper motor at 1.5 million revolutions per minute could produce a vibration of the magnetic rod, and thus the entire MPT, of 25 kHz. FIGS. 13-14 illustrate two examples of stepper motor control apparatuses that can be used as an ultrasonic signal generator. FIG. 13 is a schematic diagram of the UCN 5804 stepper motor control driver 1300 manufactured by Allegro® MicroSystems, Inc. An ultrasonic signal generator can include such a programmable driver, with a stepper motor control circuit and/or electrical conductors connecting the coils of a handpiece and the driver 1300. Returning to handpiece 300 of FIGS. 3 and 4A-4B, for example, the four outputs (1301, 1303, 1306, 1308) of the stepper motor control driver 1300 can be connected to one end of each of the four coils (304A-304D), more easily seen in FIGS. 4A-4B, instead of the four motor windings, or phases, of a stepper motor (not shown) to selectively energize the coils with the pulse generation of the driver. The other end of each coil (304A-304D) can be connected to a ground, which can be common.

Further a stepper motor control circuit can operate more than four coils and/or can operate any number of phases. Any plurality of coils can be wired to produce a phase. The element titled "LOGIC" allows a user to program the driver 1300, for example, to provide half-step excitation or other excitation as is known to one of ordinary skill in the art. A program can be created for each tip, magnetic rod, and/or handpiece. Such stepper motor control software and programming is known by those of ordinary skill in the art. An ultrasonic signal generator can include multiple stepper motor control apparatuses, such as a driver 1300 and any resulting circuitry, to controllably energize an ultrasonic tool.

FIG. 14 is a schematic diagram of a stepper motor control circuit 1400. The circuit 1400 includes another embodiment of a stepper motor driver 1402. An example of a driver 1402 is the PIC16F84 8 bit Microcontroller, produced by MicroChip Technology, Inc. The circuitry in FIG. 14 can operate an MPT at frequencies from 20 kHz to 80 kHz. In stepper motor use, the driver 1402 is connected to a stepper motor 1404, that includes a central rotor 1406 and four coils (1408, 1410, 1412, 1414) that are controlled by driver 1402, as is know in the art. To use with the ultrasonic tool of the present invention, the magnetic rod (102, 702A, 702B, 820) is substituted for the central rotor 1406 and the stepper motor coils (1408, 1410, 1412, 1414) are replaced by the handpiece coils, for example coils (304A-304D) of FIGS. 3 and 4A-4B. A user then can operate the circuit 1400 as a stepper motor control apparatus, however, the magnetic rod can be made to vibrate, instead of rotating a stepper motor, by controlling the current pulses. Optional switches 1416 are added to allow a user to further control the stepper motor control circuit 1400. Switch one 1418 will incrementally increase a delay variable, thereby slowing the vibration of the magnetic rod. Switch two 1420 increases the delay variable which increases the frequency of vibration. Switch three 1422 halts all operation while the switch is connected. Switch four 1424 reverses direction of the motor when used as a stepper motor, and thus can allow a different pattern of vibration, depending on the tip and/or magnetic rod, when used as an ultrasonic signal generator in the present invention. The driver 1402 is connected to each coil (1408, 1410, 1412, 1414) with a hex buffer chip 1426 and a transistor with a built-in diode 1428 therebetween. The stepper motor control driver 1300 of FIG. 13 can be used in the circuit 1400 of FIG. 14, in addition to the driver 1402 shown, to simplify the stepper motor control software programming, as the driver 1300 of FIG. 13 includes such built in programs as half-stepping, for example. The step angle and/or any ramping can also be varied, as is know to those skilled in the art.

The outputs (1432, 1434) from the driver 1402 can be connected to the second driver 1300 (the UCN5804 of FIG. 13). One output 1432 is connected to the step input pin 1311 and the other output 1434 is connected to the output enable pin 1315, which enables the stepper motor, which is preferably replaced with an MPT and a handpiece, while in the high position and disables the stepper motor while in the low position.

The circuitry and/or drivers in FIGS. 13-14 are for illustrative purposes, and any ultrasonic signal generator that is cable of supplying and/or varying the electrical current, and thus the geometry of the electromagnetic field, within a coil can be utilized. Each coil, or set of coils, can have its own separate ultrasonic signal generator.

While the invention has been described with respect to a limited number of embodiments, those skilled in the art will appreciate numerous modifications and variations therefrom. It is intended that the appended claims cover all such modifications and variations as fall within the true spirit and scope of the invention.

What is claimed is:

1. A precision electromagnetic ultrasonic tool comprising:
   a handpiece including a well and a plurality of coils capable of generating an electromagnetic field:
      each coil of the plurality of coils having a longitudinal axis disposed in parallel with a longitudinal, center axis of the well, the longitudinal axis of the each coil being radially offset from the longitudinal, center axis of the well, and
      each coil of the plurality of coils extending substantially from a proximal end to a distal end of the well;
   a movable magnetic rod positioned adjacent the coils for three-dimensional displacement in response to variations in the electromagnetic field;
   a tip rigidly attached to an end of the magnetic rod; and
   an ultrasonic signal generator operatively connected to the plurality of coils and configured to selectively power each of the plurality of coils to generate and control the variations in the electromagnetic field.

2. The precision electromagnetic ultrasonic tool of claim 1, wherein the ultrasonic signal generator is configured to selectively power each of the plurality of coils to generate the variations in the electromagnetic field via a computer program.

3. The precision electromagnetic ultrasonic tool of claim 1, wherein:
   a first coil of the plurality of coils provides feedback based on a current produced in the first coil while the first coil is unpowered; and
   the ultrasonic signal generator is further configured to adjust the selective powering of the each of the plurality of coils based on the feedback.

4. The precision electromagnetic ultrasonic tool of claim 1, wherein the ultrasonic signal generator is a first ultrasonic signal generator of a plurality of ultrasonic signal generators, wherein each ultrasonic signal generator of the plurality of ultrasonic signal generators is operatively connected to a respective coil of the plurality of coils.

5. An ultrasonic tool comprising:
   a handpiece providing a well and containing at least two coils conductively connected to an ultrasonic signal generator to create an anisotropic electromagnetic field in the well:
      each coil of the at least two coils having a longitudinal axis disposed in parallel with a longitudinal, center axis of the well, the longitudinal axis of the each coil being radially offset from the longitudinal, center axis of the well, and
      each coil of the at least two coils extending substantially from a proximal end to a distal end of the well;
   a magnetic rod with a distal end comprising a tip and a proximal end moveably disposed at least partially within the anisotropic electromagnetic field to vibrate the tip in a three-dimensional pattern, wherein at least one of a geometric pattern or an amplitude of the three-dimensional pattern is controlled based on a software program and corresponding to variations in the anisotropic electromagnetic field; and
   a control apparatus included in the ultrasonic signal generator to move the tip in the three-dimensional pattern, the control apparatus including a programmable driver coupled to each of the at least two coils, and the software program executable by the programmable driver to selectively energize each of the at least two coils to produce the variations in the anisotropic electromagnetic field.

6. The ultrasonic tool of claim 5 wherein the magnetic rod is tapered from a larger distal end to a smaller proximal end.

7. The ultrasonic tool of claim 5 wherein a transverse cross-section of the magnetic rod is ovate.

8. The ultrasonic tool of claim 5 wherein a transverse cross-section of the well is ovate.

9. The ultrasonic tool of claim 5 wherein each of the coils is separately connected to the ultrasonic signal generator.

10. The ultrasonic tool of claim 5 wherein each of the coils is connected to a separate ultrasonic signal generator.

11. The ultrasonic tool of claim 5 wherein the at least two coils are disposed within a wall of the handpiece between the well and an outer surface of the handpiece.

12. The ultrasonic tool of claim 5 wherein the proximal end of the magnetic rod is disposed entirely within the well.

13. The ultrasonic tool of claim 5 wherein the magnetic rod is vibratably retained within the handpiece by a friction fit between an outer surface of the magnetic rod and an inner surface of the well to form a fulcrum between the proximal and distal ends of the magnetic rod.

14. The ultrasonic tool of claim 13 further comprising a positioning tab and a corresponding positioning notch formed between the outer surface of the magnetic rod and an inner surface of the well to restrict relative rotation therebetween.

15. The ultrasonic tool of claim 13 further comprising a sealing member between the outer surface of the magnetic rod and the inner surface of the well to form a fluid-tight seal there between.

16. The ultrasonic tool of claim 5 further comprising a source of motive fluid in communication with an aperture in the tip.

17. The ultrasonic tool of claim 5 further comprising a channel in the magnetic rod in communication with an aperture in the tip and in communication with a fluid supply channel in the handpiece.

18. The ultrasonic tool of claim 5 further comprising a gripping element disposed between the magnetic rod and the tip to form a fulcrum between the proximal and distal ends of the magnetic rod.

19. The ultrasonic tool of claim 5 wherein the tip is removably attached to the distal end of the magnetic rod.

20. The ultrasonic tool of claim 5 further comprising a metallic element disposed within the at least two coils along a longitudinal axis.

21. The ultrasonic tool of claim 5 wherein the magnetic rod comprises a ferromagnetic material.

22. The ultrasonic tool of claim 5 wherein the tip comprises a dental or surgical tip.

23. The ultrasonic tool of claim 5, wherein:
a first coil of the at least two coils provides feedback based on a current produced in the first coil while the first coil is unpowered; and
the ultrasonic signal generator is further configured to adjust a selective powering of each of the at least two coils based on the feedback.

24. The precision electromagnetic ultrasonic tool of claim 5, wherein the ultrasonic signal generator is a first ultrasonic signal generator of a plurality of ultrasonic signal generators, wherein each ultrasonic signal generator of the plurality of ultrasonic signal generators is operatively connected to a respective coil of the at least two coils.

25. A method of vibrating a tip of an ultrasonic tool comprising:
affixing the tip to a magnetic rod;
positioning the magnetic rod on a fulcrum disposed between the tip and a plurality of electromagnetic coils contained within a well of a handpiece:
each coil of the plurality of electromagnetic coils having a longitudinal axis disposed in parallel with a longitudinal, center axis of the well of the handpiece, the longitudinal axis of the each coil being radially offset from the longitudinal, center axis of the well, and
each coil of the plurality of electromagnetic coils extending substantially from a proximal end to a distal end of the well;
controllably and selectively energizing at least one of the plurality of electromagnetic coils to generate an anisotropic electromagnetic field; and
controlling a frequency, an amplitude and a geometry of each dimension of a three-dimensional displacement of the magnetic rod and the tip to vary based on variations in the anisotropic electromagnetic field.

26. The method of claim 25, further comprising:
providing, by a first coil of the plurality of electromagnetic coils, feedback based on a current produced in the first coil while the first coil is unpowered; and
adjusting a selective powering of each of the plurality of electromagnetic coils based on the feedback.

27. A method of vibrating a tip of an electromagnetic ultrasonic tool comprising:
vibratably retaining a magnetic rod within a well of a handpiece of the electromagnetic ultrasonic tool, wherein the tip is adjacent an entry to the well and is attached to an end of the magnetic rod;
connecting an ultrasonic signal generator to an energy source and to a plurality of electromagnetic coils disposed within the handpiece to provide an electromagnetic field:
each coil of the plurality of electromagnetic coils having a longitudinal axis disposed in parallel with a longitudinal, center axis of the well of the handpiece, the longitudinal axis of the each coil being radially offset from the longitudinal, center axis of the well, and
each coil of the plurality of electromagnetic coils extending substantially from a proximal end to a distal end of the well; and
controlling at least one of a vibration of the tip at a desired amplitude or the vibration of the tip in a desired geometric pattern solely by varying the energy to at least one of the electromagnetic coils with a control apparatus included in the ultrasonic signal generator, the control apparatus including a programmable driver coupled to each of the at least one of the electromagnetic coils and a software program executable by the programmable driver to selectively power each of the at least one of the electromagnetic coils to change the electromagnetic field with the ultrasonic signal generator to displace the magnetic rod.

28. The method of claim 27 further comprising applying the tip to impact or penetrate a substrate.

29. The method of claim 27 further comprising applying the tip to clean, cut, polish, abrade or massage a dental surface.

30. The method of claim 27, wherein:
providing, by a first coil of the plurality of electromagnetic coils, feedback based on a current produced in the first coil while the first coil is unpowered; and
adjusting a selective powering of each of the plurality of electromagnetic coils based on the feedback.

31. The method of claim 27, wherein the ultrasonic signal generator is a first ultrasonic signal generator of a plurality of ultrasonic signal generators, wherein each ultrasonic signal generator of the plurality of ultrasonic signal generators is operatively connected to a respective coil of the plurality of electromagnetic coils.

32. A precision electromagnetic ultrasonic tool comprising:
   a handpiece including a well;
   an insert retained in the handpiece comprising a proximal movable pin transducer rigidly carrying a distal working tip;
   ultrasonic drive means comprising:
      a plurality of coils in the handpiece to generate an electromagnetic field of chronologically varying anisotropy adjacent a magnetic pin of the moveable pin transducer for repetitively moving the pin in response to the chronologically varying anisotropy of the electromagnetic field:
         each coil of the plurality of coils having a longitudinal axis disposed in parallel with a longitudinal, center axis of the well, the longitudinal axis of the each coil being radially offset from the longitudinal, center axis of the well, and
         each coil of the plurality of coils extending substantially from a proximal end to a distal end of the well,
      a first ultrasonic drive signal to selectively energize each of the plurality of coils to generate a first electromagnetic field of a first chronologically varying anisotropy, thereby vibrating the working tip in a first pattern of motion defined by the first ultrasonic drive signal, and
      a second ultrasonic drive signal to selectively energize each of the plurality of coils to generate a second electromagnetic field of a second chronologically varying anisotropy; thereby vibrating the working tip in a second pattern of motion defined by the second ultrasonic drive signal.

33. The precision electromagnetic ultrasonic tool of claim 32, wherein:
   a first coil of the plurality of coils provides feedback based on a current produced in the first coil while the first coil is unpowered; and
   the ultrasonic drive means is further configured to adjust the selective energizing of the each of the plurality of coils based on the feedback.

* * * * *